United States Patent [19]

Rule et al.

[11] Patent Number: 4,814,525

[45] Date of Patent: Mar. 21, 1989

[54] VAPOR PHASE BROMINATION OF AROMATIC COMPOUNDS

[75] Inventors: Mark Rule; Donald W. Lane, Larkins; Thomas H.; Gerald C. Tustin, all of Kingsport, Tenn.

[73] Assignee: Eastman Kodak Company, Rochester, N.Y.

[21] Appl. No.: 29,951

[22] Filed: Mar. 25, 1987

[51] Int. Cl.$^4$ .................... C07C 17/15; C07C 17/152
[52] U.S. Cl. .................................. 570/203; 570/206; 570/208
[58] Field of Search ................... 570/203, 206, 208

[56] References Cited

FOREIGN PATENT DOCUMENTS

| 20126 | 2/1974 | Japan | 570/206 |
|---|---|---|---|
| 0224645 | 11/1985 | Japan | 570/206 |
| 0825479 | 4/1981 | U.S.S.R. | 570/206 |
| 1411524 | 10/1975 | United Kingdom | 570/206 |

OTHER PUBLICATIONS

NL,A, 6609732, Jan. 15, 1968.
FR,A, 2187735, Jan. 18, 1974.
Chemical Abstract, vol. 104, No. 21, May 1986, p. 604, Abstract No. 186110e.
Chemical Abstract, vol. 95. No. 7, Aug. 1981, p. 675, Abstract No. 61724x.

*Primary Examiner*—Werren B. Lone
*Attorney, Agent, or Firm*—Charles R. Martin; William P. Heath, Jr.

[57] ABSTRACT

The process relates to a process for the vapor phase bromination of aromatic compounds in the presence of oxygen and a catalyst comprising an oxidizing metal and an inert support.

16 Claims, No Drawings

VAPOR PHASE BROMINATION OF AROMATIC COMPOUNDS

BACKGROUND OF THE INVENTION

1. Field of the Invention

The present invention relates to a process for the vapor phase oxidative bromination of aromatic compounds using a metal catalyst on a support such as a zeolite.

2. Discussion of the Background

The bromination of aromatic compounds is traditionally carried out by electrophilic substitution reactions using aromatic substrates such as benzene or naphthalene. The most common catalysts are the bromides of iron or aluminum although many other catalysts including iodine are effective. These reactions are generally known as Friedel-Crafts reactions.

Halogenation of aromatic compounds can also be carried out by an oxidative halogenation process. Vapor phase oxidative chlorination of aromatics is a commercial process and has been described in U.S. Pat. Nos. 1,963,761; 3,303,223; 3,389,186 and 3,644,542. In contrast, the vapor phase oxybromination of aromatics has received little attention, although liquid phase oxybromination is known. See for example U.S. Pat. No. 4,380,682 which discloses the oxybromination of aliphatic hydrocarbons by first performing a non-selective oxyhalogenation given intermediate partially halogenated product which is then reacted with bromine gas in the absence of oxygen over a silica-alumina catalyst to give the final product.

U.S. Pat. No. 3,591,645 discloses the oxybromination of aromatic compounds, preferably benzene and toluene by heating the substrates in an inert solvent in the presence of bromides and a compound containing nitrate ions. The oxybromination is carried out over a catalyst which is suspended in the solvent and is preferably an oxidizing metal such as copper, manganese, cobalt, vanadium, etc.

Other liquid phase oxybrominations of aromatic compounds are known which use iron or copper salts to effect bromination. See Japanese Nos. 49/18832 and 49/18831. Additionally, the use of molucular sieves to increase para-selectivity in liquid activity phase brominations is described in J. Catal., 60, 110 (1979).

A need still exists, however, for an efficient and selective method for the vapor phase oxybromination of aromatic compounds.

SUMMARY OF THE INVENTION

Accordingly, one object of the present invention is to provide a method for the vapor phase oxybromination of aromatic compounds which can be carried out over readily available catalysts.

Another object of the invention is to provide a method for the vapor phase oxybromination of aromatic compounds which is selective for para-brominated products.

Still a further object of the invention is to provide a method which has a selectivity similar to liquid phase bromination.

These objects and other objects of the present invention which will become apparent from the following specification have been achieved by the present method for brominating an aromatic compound which comprises reacting a source of bromine in the presence of a source of oxygen over a metal catalyst supported on a solid support.

DESCRIPTION OF THE PREFERRED EMBODIMENTS

The aromatic compounds which can be utilized in practice of the present invention are essentially any aromatic compound including substituted and unsubstituted aromatics. Suitable aromatic compounds include hydrocarbon aromatics, nitrogen containing aromatics and sulfur containing aromatics. Typical hydrocarbon aromatics include benzene and biphenyl, condensed ring aromatics such as naphthalene and anthracene, sulfur containing aromatics including thiophene, benzothiophene, nitrogen containing aromatics such as pyridine and benzopyridine and substituted aromatics such as sulfones, diaryl ethers, diaryl carbonyls, diaryl sulfides and the like. Aromatic compounds substituted by alkyl groups are generally not preferred for utilization in the present technique. It has been found that alkyl substituted aromatics are not only brominated by the present catalyst system but also oxidized as well and further that the bromination reaction is not limited to the aromatic ring but that one obtains a mixture of products. That is, the products are brominated not only on the ring but also on the side chains. Further, the product obtained will also contain oxidized side chains and the like. Thus, while alkyl substituted aromatics can be utilized in the present technique their use is not preferred. Substituents which may be present include phenyl, fluoro, bromo, iodo, chloro, cyano, and hydroxyl substituents.

Specific aromatic compounds which can be utilized in the present invention include benzene, biphenyl, terphenyl, naphthalene, benzophenone, diphenyl sulfone, diphenyl ether, chlorobenzene, fluorobenzene, chloronaphthalene, benzonitrile, phenol, 1-naphthol, 2-naphthol, pyridine, chloropyridine, and iodobenzene.

The catalyst used in the present method comprises an oxidizing metal and a solid support. The oxidizing metal may be a wide variety of transition metals. Preferred metals include copper, iron, molybdenum, manganese, chromium, vanadium, nickel, cobalt, and mixtures thereof. More preferred metals are copper and iron, with iron being the most preferred metal catalyst.

The solid support may be acidic or non-acidic and may be comprises of a wide variety of solid inert support materials. Typical examples of support materials include alumina, silica, and titania. Other examples include the zeolites such as the alkali and alkaline-earth zeolites. Within the zeolites, the X-zeolites and Y-zeolites are preferred. In general, the zeolites are preferred over other inert support materials since catalysts made from zeolites are more active and exhibit more selectivity in the bromination reaction. The zeolites should have a pore size at least equal to about the apparent size of the molecule of the aromatic ring compound being reacted. Benzene as well as naphthalene have apparent ring sizes of about 6 Å and this is the lower limit on the pore size of the zeolite catalyst which is useful. If the aromatic compound cannot enter into the pore of the zeolite catalyst then only very little conversion of the aromatic compound will occur. Hence, the preferred zeolites have a pore size of about 6 Å or larger.

The catalyst comprising both the oxidizing metal and the inert solid support is generally produced by impregnating the solid support with the oxidizing metal. This impregnation process can be achieved by any method which incorporates an adequate amount of the oxidizing metal into the solid support. A preferred method is the introduction of the oxidizing metal into the solid support in the form of an aqueous salt solution of the oxidizing metal cation. In this process, the inert support and the aqueous solution of the metal salt are mixed together in an ion exchange type process. The period time over which the contact between the aqueous metal salt solution and the inert support is conducted and the number of times the ion exchange process is performed is dependent upon the degree of replacement desired. Thus, if one begins with a zeolite in the sodium form, one may ion exchange this material with another counterion to partially or substantially completely replace the sodium ion with a different counterion such as iron. Altneratively, the desired metals can be impregnated onto the support by vapor phase deposition or by contacting non-aqueous solutions of the desired metal with the support.

The counterion for the metal salt is of no particular importance and any appropriate counterion may be used. Suitable counterions include chloride, bromide, nitrate, hydroxide, carbonate, perchlorate, sulfate, or acetate.

The temperature at which the reaction is to be conducted is not critical and can be any temperature at which the aromatic compound is in the vapor phase. The maximum temperature at which the process can be carried out is that at which combustion of the aromatic compound occurs. Generally, temperatures of from 100° C. to 500° C. have been found satisfactory with temperatures of from 200°-400° C. being preferred, more preferably from about 300°-400° C. In operating at the lower ranges, the catalysts exhibit their greatest selectivity.

The pressure at which the process is conducted is not critical and can range from subatmospheric to superatmospheric. The utilization of elevated pressures in the gas phase process may be preferred so as to minimize equipment size. In general, pressures from atmospheric to about 600 psig have proven satisfactory although higher or lower pressures can be utilized.

The source of oxygen for the oxybromination reaction can be pure oxygen, air or air diluted with any other inert material, such as carbon dioxide or water vapor. Essentially, oxygen from any convenient source may be utilized. The purpose of the oxygen is to regenerate the active site of the zeolite catalyst to its active form once the bromination reaction has occurred. Thus the amount of oxygen present during the reaction is not critical. However, it is preferred that at least one-half mole of oxygen be used for every mole of bromine measured as $Br_2$ or HBr. Greater or lesser quantities of bromine can be utilized as one desires. The utilization of large excesses of bromine result in a product which is contaminated with unreacted bromine. When all the bromine is reacted, a colorless product is obtained. In general, it is desired to run the process to obtain as close as 100% conversion of the bromine as practical so as to simplify the purification steps in the recovery of any unreacted bromine. Suggested molar ratios of starting materials material to bromine to oxygen are from 1:0.5:0.25 to about 1:2:3. However, other ratios may be utilized as desired. The molar ratio of bromine to starting material is not critical.

Essentially, any source of bromine may be employed including $Br_2$, HBr, and alkyl bromides. The alkyl bromides are generally lower alkyl bromides. By "lower alkyl" is meant alkyl groups having 1-8 carbon atoms, preferably 1-4 carbon atoms. The alkyl group may be straight chain, branched or cycloaliphatic. Specific examples include methyl bromide, ethyl bromide, propyl bromide, n-butyl bromide, pentyl bromide, hexyl bromide and cyclohexyl bromide. Methyl bromide is the preferred alkyl bromide employed. The HBr may be utilized as an aqueous solution, preferably 48%, although solutions having other concentrations of HBr may be used satisfactorily. It is necessary to vaporize the aqueous HBr before it contacts the catalyst.

It is anticipated by the present process would be carried out continuously by the continuous addition of bromine, oxygen and starting materials to the reactor, however, the process can be carried out on as batch or semi-batch processes desired. Further, starting materials and bromine can be reacted over the catalyst to produce the brominated product, the addition of starting materials and bromine then being terminated and oxygen then added to the reactor to regenerate the catalyst to its active form and then the process commenced again. Alternatively, in a continuous process it is possible to utilize two reactants circulating the catalyst between them. In the first reactor the bromine and aromatic compound would be added and reacted to form the brominated compound. The catalyst would then be circulated to the second reactor where it would be contacted with oxygen to be regenerated and then recycled to the first reactor to catalyze additional reactions of aromatic compound with bromine.

The space velocity of the process is not critical and may be readily selected by the artisan. Gas hourly space velocity is between 10 to 50,000, preferably between 100 and 20,000 liters per hour of reagents per liter of active zeolite have proven satisfactory.

The catalyst is proven to have an extemely long life and degrades only slowly with time. The degradation of the catalyst is believed to be caused by the combustion of very small quantities of the aromatic compound which deposits small quantities of carbon on the active sites thereby degrading the catalyst activity. When the reaction conditions are selected such that none of the aromatic starting material is oxidized, the life of the catalyst is essentially indefinite. However, when the catalyst becomes deactivated reactivation is simple. An excellent regeneration technique comprises passing air or oxygen over the catalyst for several hours at elevated temperatures. Typically the temperature is above 400° C. although higher or lower temperatures are proven equally satisfactory. The temperature need only be high enough so as to ensure combustion of the carbon deposit on the catalyst. When pure oxygen is employed lower temperatures can be utilized, while when air is employed temperatures on the order of about 400° C. have proven satisfactory.

Other features of the invention will become apparent in the course of the following descriptions of exemplary embodiments which are given for illustration of the invention and are not intended to be limiting thereof.

EXAMPLES

In the following examples, 25 cc of the stated catalyst was placed in a vycor reactor tube with an internal thermowell. The tube was heated with an electric furnace while the reactants were added dropwise over the catalyst bed at the specified rate. Air was fed cocurrently at 300 ml/min. Products were collected by condensing against cold water and identified by gas chromotography-mass spectrometry and quantified by gas chromotography (reported as mole %).

EXAMPLE 1

Catalyst: Fe-Silica-alumina
Furnace temp: 300° C.
Reaction temp: 351° C.
Aromatic feed: benzene at 0.5 ml/min
Bromine feed: 48% aq HBr at 0.5 ml/min The reaction product contained 59.0% benzene, 31.7% bromobenzene, and 8.8% dibromobenzenes (o:m:p=31:3:66). The bromine conversion was 60%.

EXAMPLE 2

Catalyst: Cu-Silica-alumina
Furnace temp: 300° C.
Reaction temp: 342° C.
Aromatic feed: benzene at 0.5 ml/min
Bromine feed: 48% aq HBr at 0.5 ml/min The reaction product contained 65.2% benzene, 27.0% bromobenzene, and 6.6% dibromobenzenes (o:m:p=32:4:66). The bromine conversion was 49%.

EXAMPLE 3

Catalyst: Fe-NaX
Furnace temp: 300° C.
Reaction temp: 305° C.
Aromatic feed: 1-bromonaphthalene at 0.5 ml/min
Bromine feed: liquid bromine at 0.1 ml/min The reaction product contained 24.7% bromonaphthalene, 57.4% dibromonaphthalenes, and 17.9% tribromonaphthalenes. Bromine conversion was 93%.

In the following examples, benzene, aqueous HBr, and air are fed at the specified ratios over 25 cc of Fe—NaX catalyst.

presence of molecular oxygen over a catalyst comprising an oxidizing transition metal and a alumina, silica or titania solid support.

2. The process of claim 1, wherein the source of bromine comprises a member selected from the group consisting of $Br_2$, HBr and alkylbromides.

3. The process of claim 1, wherein the source of oxygen comprises $O_2$, air or a mixture of oxygen and an inert gas.

4. The process of claim 1 wherein said catalyst contains an oxidizing transition metal selected from the group consisting of copper, iron, molybdenum, manganese, chromium, vanadium, nickel, cobalt, and mixtures thereof.

5. The process of claim 1, wherein said catalyst contains copper or iron.

6. The process of claim 1, wherein said aromatic compound is benzene.

7. The process of claim 1, wherein said aromatic compound is naphthalene.

8. The process of claim 1, wherein said process is carried out at temperatures between about 150°-500° C.

9. The process of claim 7, wherein said process is carried out at temperatures between about 200°-400° C.

10. A process for the vapor phase mono-, di- or tribromination of an aromatic compound which comprises reacting bromine with an aromatic compound selected from the group consisting of benzene, biphenyl, naphthalene, anthracene, thiophene, benzothiophene, benzopyridine, terphenyl, benzophenone, diphenyl sulfone, diphenyl ether, chlorobenzene, fluorobenzene, chloronaphthalene, benzonitrile, phenol, 1-naphthol, 2-naphthol, pyridine, chloropyridine and iodobenzene in the presence of molecular oxygen over a catalyst comprising an oxidizing transition metal selected from the

| Example No. | Feed Molar Ratio | | | Bed Temp, °C. | Contact Time, sec | Benzene Oxybromination Yield Data | | | | | | | m/p/o, % | $CO_2$, % | $O_2$, % |
|---|---|---|---|---|---|---|---|---|---|---|---|---|---|---|---|
| | | | | | | % Conversion | | Space Time Yield, $gl^{-1} hr^{-1}$ | | | | | | | |
| | ½[$O_2$] | HBr | φH | | | φH | HBr | monobromo | meta | para | ortho | tribromo | | | |
| 4 | 1.0 | 1.0 | 1.0 | 362 | .65 | 56 | 87 | 716 | 17 | 184 | 59 | 14 | 6/71/23 | .191 | 4.150 |
| 5 | 1.0 | 1.0 | .5 | 348 | .70 | 68 | 82 | 410 | 13 | 148 | 49 | 16 | 6/71/23 | .111 | 6.340 |
| 6 | .5 | .5 | .5 | 345 | 1.34 | 78 | 98 | 410 | 13 | 157 | 45 | 11 | 6/73/21 | .247 | 3.313 |
| 7 | .5 | 1.0 | 1.0 | 345 | .77 | 26 | 50 | 496 | 5 | 44 | 17 | 1 | 8/67/25 | .240 | 1.390 |
| 8 | .5 | 1.0 | .5 | 344 | .83 | 54 | 50 | 241 | 4 | 35 | 14 | 2 | 8/66/26 | .167 | 1.205 |
| 9 | 1.0 | .5 | .5 | 349 | 1.05 | 88 | 99.8 | 331 | 14 | 212 | 52 | 24 | 5/76/19 | .184 | 7.620 |
| 10 | .5 | .5 | 1.0 | 351 | 1.19 | 48 | 99.7 | 585 | 8 | 92 | 26 | 3 | 6/73/21 | .396 | 1.806 |
| 11 | 1.0 | .5 | 1.0 | 349 | .96 | 60 | 99.9 | 530 | 7 | 101 | 25 | 4 | 5/76/19 | .257 | 7.421 |

Obviously, numerous modifications and variations of the present invention are possible in light of the above teachings. It is therefore to understand that within the scope of the appended claims, the invention may be practiced otherwise than as specifically described herein.

What is claimed as new and desired to be secured by Letters Patent of the United States is:

1. A process for the vapor phase mono-, di-, or tribromination of an aromatic compound which comprises reacting bromine with an aromatic compound selected fromthe group consisting of benzene, biphenyl, naphthalene, anthracene, thiophene, benzothiophene, benzopyridine, terphenyl, benzophenone, diphenyl sulfone, diphenyl ether, chlorobenzene, fluorobenzene, chloronaphthalene, benzonitrile, phenol, 1-naphthol, 2-naphthol, pyridine, chloropyridine and iodobenzene in the group consisting of iron, molybdenum, manganese, chromium, vanadium, nickel, cobalt and mixtures thereof and a solid zeolite support.

11. The process of claim 10, wherein said zeolite is an X-zeolite or Y-zeolite.

12. The process of claim 11, wherein said zeolite is an alkali or alkaline-earth containing zeolite.

13. The process of claim 10, wherein said catalyst contains iron.

14. The process of claim 10, wherein said aromatic compound is benzene.

15. The process of claim 10, wherein said aromatic compound is naphthalene.

16. The process of claim 10, wherein said process is carried out at temperatures between about 150°-500° C.

* * * * *